United States Patent [19]

Merger et al.

[11] 4,322,365

[45] Mar. 30, 1982

[54] PREPARATION OF ISOCYANATES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 265,156

[22] Filed: May 19, 1981

[30] Foreign Application Priority Data

Jun. 6, 1980 [DE] Fed. Rep. of Germany ....... 3021299

[51] Int. Cl.$^3$ ............................................ C07C 118/00
[52] U.S. Cl. ................................................. 260/453 P
[58] Field of Search ...................................... 260/453 P

[56] References Cited

U.S. PATENT DOCUMENTS 3,734,941  5/1973  Sydor ............................... 260/453 P

*Primary Examiner*—Dolph H. Torrence
*Attorney, Agent, or Firm*—John H. Shurtleff

[57] ABSTRACT

Isocyanates are prepared by thermal decomposition of oxalic acid ester amides at not less than 300° C.

The isocyanates obtainable by the process of the invention are valuable starting materials for the preparation of crop protection agents, pesticides, dyes, synthetic resins, plastics, textile waterproofing agents, detergents and adhesives.

7 Claims, No Drawings

PREPARATION OF ISOCYANATES

The present invention relates to a process for the preparation of isocyanates by thermal decomposition of oxalic acid ester amides at not less than 300° C.

Isocyanates are in general prepared by phosgenation of primary amines (Houben-Weyl, Methoden der Organischen Chemie, Volume VIII, page 119-121), but this process has severe disadvantages because of the toxicity of phosgene, the corrosiveness of HCl, and the resulting expense of carrying out the process industrially. Thus, the investment costs are high, particularly where relatively small amounts of isocyanates are to be manufactured.

German Laid-Open Application DOS No. 1,593,554 discloses the preparation of isocyanates from carbamyl chlorides in the presence of an organic base, such as a tertiary amine, or of an N,N-dialkylcarboxamide in an organic solvent. Isocyanates can also be obtained by using an aqueous solution or suspension of an inorganic base, such as an alkali metal hydroxide, alkaline earth metal hydroxide, alkali metal carbonate, alkaline earth metal carbonate or alkali metal bicarbonate (British Pat. No. 1,208,862). U.S. Pat. No. 3,465,023 points out explicitly that the formation of hydrogen chloride during preparation of an isocyanate reduces the reactivity of the end product and that therefore it is important to bind the acid during the process. The distillation of the isocyanate also presents difficulties, and corrosion of the equipment occurs. The processes mentioned have the disadvantage that the isocyanate is formed in a medium in which it is prone to decompose. Thus, it is known from Houben-Weyl, Methoden der Organischen Chemie, Volume VIII, page 136 (1952) that isocyanates dimerize in the presence of tertiary amines. They are extremely unstable to aqueous alkali and even if only a stoichiometric amount of aqueous alkali is used, they are converted to a large extent to carbamates or carbamic acids.

German Pat. No. 1,193,034 discloses a process wherein N-alkylcarbamyl chlorides, alkyl being of 1 to 3 carbon atoms, are decomposed in an organic solvent, the hydrogen chloride formed being removed from the reaction zone via a reflux condenser and the alkyl isocyanate formed being removed at the same time by distillation through a column. The solvent must have a boiling point not less than 10° C. above the boiling point of the alkyl isocyanate formed. It is pointed out that an isocyanate whose boiling point is below the decomposition point of the corresponding carbamyl chloride cannot be prepared by refluxing the carbamyl chloride; examples of such isocyanates are the alkyl isocyanates. The Patent states that whilst in such cases the carbamyl chloride may be decomposed thermally, an equilibrium results and a large proportion of the hydrogen chloride recombines with the isocyanate formed, to reconstitute the starting material.

More recently, attempts have been made to develop cheaper processes, with fewer problems, for the synthesis of isocyanates. For example, it has been proposed to prepare aromatic isocyanates directly from the corresponding nitro compounds and carbon monoxide, using a noble metal catalyst (German Pat. Nos. 1,815,517, 1,909,190 and 1,944,747). However, this process is only useful for aromatic isocyanates and entails substantial expense because of the noble metal catalyst employed.

A further method of arriving at isocyanates is the thermal cleavage of urethanes (German Laid-Open Applications Nos. DOS 2,635,490 and DOS 2,410,505), which are obtained from nitro compounds, carbon monoxide and alcohol (German Laid-Open Application DOS No. 2,623,694, European Patent Application No. 0,000,563, and German Laid-Open Application No. NOS 2,614,101). This process has hitherto also only been used for aromatic isocyanates and is furthermore expensive, since the preparation of the urethane intermediates necessitates high pressures and the use of catalysts which are either very expensive, for example noble metals, or may form toxic by-products, for example selenium compounds. It has also already been proposed to prepare urethanes by reacting diaryl carbonates, di-(alkylaryl) carbonates or dialkyl carbonates with amines (German Laid-Open Application No. DOS 2,160,111). However, when this process is applied to the formation of aromatic urethanes, the space-time yields are only moderate and furthermore the reaction has to be conducted carefully since otherwise substantial amounts of alkylated amines are formed as by-products. All these processes are accordingly unsatisfactory in respect of economical and simple operation, inexpensive equipment and easily accessible starting materials.

We have found that an isocyanate of the formula $$R^1 13 \, N=C=O \qquad \qquad I$$

where $R^1$ is an aliphatic, cycloaliphatic, araliphatic, aliphatic-aromatic or aromatic radical, is obtained in an advantageous manner by thermal cleavage of carboxamido compounds if an oxalic acid ester amide of the formula

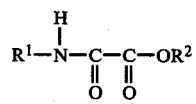

where $R^1$ has the above meanings and $R^2$ is an aliphatic, cycloaliphatic, araliphatic, aliphatic-aromatic or aromatic radical, is cleaved thermally at not less than 300° C.

Where oxalic acid methyl ester N-phenylamide is used, the reaction can be represented by the following equation:

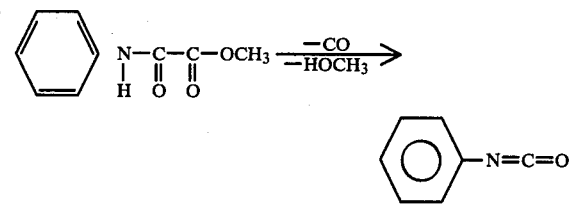

Compared to the conventional processes, the process according to the invention gives isocyanates more simply and more economically, in very good yield and very high purity. Compared to the process described in German Pat. No. 1,193,034, the process according to the present invention is safer in operation. Elimination and removal of a toxic hydrogen halide are avoided, and accordingly the safety of both the process and the operating personnel is greater. The difficulties in respect of distillation, corrosion problems and reduced reactivity of the end products, mentioned in the U.S. Patent referred to, do not arise to a significant degree. The process does not require expensive solvents or additional bases. These advantageous results are surprising since, from the prior art, it was in particular to be expected that polymers or decomposition products would form under the high temperatures employed in the present invention. Compared to the starting materials used in the processes mentioned above, namely urethanes or nitro compounds, the starting materials used according to the present invention, namely amines and oxalic acid esters, are more easily obtainable. Furthermore, it is an advantage that the process avoids toxic and corrosive chlorocarbonic acid esters, expensive selenium-catalyzed or noble metal-catalyzed reductive carbonylation of nitro compounds (entailing high pressures, toxic carbon monoxide, and toxic or expensive catalysts), and involved reactions of amines with dimethyl carbonate (which form numerous by-products).

The oxalic acid ester amides employed as starting materials II can easily be prepared, for example by reacting amines with dialkyl oxalates. Preferred starting materials II, and accordingly preferred end products I, are those where $R^1$ is alkyl of 1 to 18, especially of 1 to 10, carbon atoms, cycloalkyl of 5 to 8 carbon atoms, aralkyl or alkylaryl of 7 to 12 carbon atoms or phenyl which is unsubstituted or substituted by one or two chlorine atoms and/or alkoxy groups of 1 to 4 carbon atoms. The above radicals can additionally be substituted by groups and/or atoms which are inert under the reaction conditions, for example alkyl, alkylmercapto, alkoxy, alkylamino or dialkylamino (alkyl in each case being of 1 to 5 carbon atoms), cyano, nitro, bromine and chlorine.

Examples of suitable starting materials II are methyl, ethyl, n-propyl, iso-propyl, n-butyl, sec.-butyl, tert.-butyl, 2-methylbut-1-yl, 3-methylbut-1-yl, 2-methylbut-2-yl, 3-methylbut-2-yl, pent-1-yl, pent-2-yl, pent-3-yl, neo-pentyl, n-hexyl, n-octyl, decyl, cyclopentyl, cyclohexyl, benzyl and phenyl esters of oxalic acid monomethylamide; phenyl esters of oxalic acid monomethylamide, in which phenyl is monosubstituted in the 2-, 3- or 4-position or disubstituted in the 2,3-, 2,4-, 2,5-, 2,6-, 3,4- or 3,5-position, the substituents being chlorine, methyl, ethyl, methoxy or ethoxy, and, in the case of disubstitution, being identical or different; and homologous monoesters to the above, in which the amide group, instead of being substituted by methyl, is substituted by ethyl, n-propyl, iso-propyl, n-butyl, iso-butyl, sec.-butyl, 2-methylbut-1-yl, 3-methylbut-1-yl, 3-methylbut-2-yl, pent-1-yl, pent-2-yl, pent-3-yl, neo-pentyl, n-hexyl, n-octyl, decyl, cyclopentyl, cyclohexyl or benzyl or by phenyl which is unsubstituted or is monosubstituted in the 2-, 3- or 4-position or disubstituted in the 2,3-, 2,4-, 2,5-, 2,6-, 3,4- or 3,5-position, the substituents being chlorine, methyl, ethyl, methoxy or ethoxy and, in the case of disubstitution, being identical or different.

The reaction is advantageously carried out at from 300° to 900° C., preferably from 400° to 700° C., under reduced pressure, atmospheric pressure or superatmospheric pressure, preferably at from 0.001 to 40 bar, especially from 0.005 to 1 bar, batchwise or, preferably, continuously. Advantageously, the reaction space used is a reaction tube of diameter from 20 to 1,000 millimeters and length from 100 to 2,000 millimeters, containing packings of from 10 to 50 millimeters diameter. Examples of suitable packings are Raschig rings, glass rings, wire mesh rings, Pall rings, steel wool, iron turnings and copper turnings.

Advantageously, a solvent which is inert under the reaction conditions is employed. Examples of suitable solvents are aromatic hydrocarbons, e.g. toluene, ethylbenzene, o-, m- and p-xylene, isopropylbenzene and methylnaphthalene, and mixtures of these. The solvent is advantageously used in an amount of from 400 to 10,000 percent by weight, based on starting material II.

The reaction can be carried out as follows: the starting material, in solid, liquid or gaseous form, and mixed, if appropriate, with inert gas and/or solvent, is passed through the reaction space at the decomposition temperature. It is advantageous to pass a stripping gas through the reaction space, or apply suction, or use an inert solvent, in order to remove the cleavage products rapidly from the cleavage reactor and, where appropriate, to facilitate effective separation of the end product from the alcohol formed. Advantageously, the pressure to be used in the reactor is normally chosen in accordance with the boiling point of the reaction products, namely the isocyanate I and the alcohol. Preferably the pressures used permit the end product to be discharged rapidy from the reactor, but still allow fractional condensation. The throughput is advantageously from 10 to 500, especially from 50 to 300, grams of starting material II per liter of reaction space per hour. The end product can, where appropriate, be used direct, or can be purified in a conventional manner, for example by fractional distillation or crystallization.

The isocyanates obtainable by the process of the invention are valuable starting materials for the preparation of crop protection agents, pesticides, dyes, synthetic resins, plastics, textile waterproofing agents, detergents and adhesives. Concerning their use, reference may be made to the publications mentioned above and to Ullmanns Encyklopädie der technischen Chemie, Volume 9, pages 11, 12 and 404, and Volume 17, page 204.

In the Examples which follow, parts are by weight, and bear the same relation to parts by volume as that of the kilogram to the liter.

EXAMPLE 1

Using a metering screw, 20 parts of oxalic acid methyl ester N-phenylamide are introduced, in the course of 45 minutes, into the top of a tube reactor which has a capacity of 160 parts by volume and is packed with wire rings, and the interior of which is at 600° C. and under a pressure of 19 mbar. The lower end of the reactor terminates in a receiver which is water-cooled, and in which the phenyl isocyanate formed is condensed. This is followed by a second receiver, cooled with solid carbon dioxide, for condensing the methanol.

The conversion, determined by gas chromatography, is 78 percent, and 9.5 parts of phenyl isocyanate (91.6% of theory), of boiling point 164°–67° C. are obtained.

EXAMPLES 2 TO 8

The other Examples are carried out similarly to Example 1, but varying the starting material, temperature, time, pressure and reactor packing. The results of these reactions are shown in the Table.

| Example | Starting material | Isocyanate | Temp. °C. | Pressure mbar | Packing | Conversion % | Yield % of theory | Space-time yield, in parts by volume/liter of reaction space x hour |
|---|---|---|---|---|---|---|---|---|
| 2 | C₆H₅—NHC(O)—C(O)—OCH₃ | C₆H₅—NCO | 600 | 19 | steel wool | 71 | 84 | 97 |
| 3 | 2,6-Cl₂-C₆H₃—NHC(O)—C(O)—OCH₃ | 2,6-Cl₂-C₆H₃—NCO | 575 | 27 | wire mesh rings | 100 | 98 | 186 |
| 4 | 4-Cl-C₆H₄—NHC(O)—C(O)—OCH₃ | 4-Cl-C₆H₄—NCO | 580 | 24 | wire mesh rings | 93 | 87 | 146 |
| 5 | 4-CH₃-C₆H₄—NHC(O)—C(O)—OCH₃ | 4-CH₃O-C₆H₄—NCO | 610 | 14 | steel wool | 64 | 82 | 93 |
| 6 | C₆H₅—NHC(O)—C(O)—OC₄H₉ | C₆H₅—NCO | 590 | 15 | steel wool | 88 | 72 | 85 |
| 7 | C₈H₁₇NHC(O)—C(O)—OCH₃ | C₈H₁₇NCO | 575 | 29 | wire mesh rings | 64 | 44 | 51 |
| 8 | CH₃NHC(O)—C(O)—OC₁₀H₂₁ | CH₃NCO | 600 | 40 | wire mesh rings | 57 | 88 | 29 |

EXAMPLE 9

A solution of 200 parts of oxalic acid methyl ester N-phenylamide in 400 parts of o-xylene is introduced, in the course of 190 minutes, into a vaporizer heated to 280° C. The vapors obtained are passed, with 3 parts by volume of nitrogen per part by volume of reaction mixture through a cleavage reactor of capacity 160 parts by volume, which is packed with steel wool and has an internal temperature of 590° C. The gaseous product mixture is subjected to fractional distillation. The conversion, determined by gas chromatography, is 86%, and 93.8 parts of phenyl isocyanate (82% of theory), of boiling point 54°–55° C./17 mbar, are obtained.

We claim:

1. A process for the preparation of an isocyanate of the formula $$R^1-M=C=O \qquad \text{I}$$

where $R^1$ is an aliphatic, cycloaliphatic, araliphatic, aliphatic-aromatic or aromatic radical, by thermal cleavage of a carboxamido compound, wherein an oxalic acid ester amide of the formula $$R^1-N(H)-C(O)-C(O)-OR^2 \qquad \text{II}$$

where $R^1$ has the above meanings and $R^2$ is an aliphatic, cycloaliphatic, araliphatic, aliphatic-aromatic or aromatic radical, is cleaved thermally at not less than 300° C.

2. A process as claimed in claim 1, wherein the reaction is carried out with from 10 to 500 grams of starting material II per liter of reaction space per hour.

3. A process as claimed in claim 1, wherein the reaction is carried out at from 300° to 900° C.

4. A process as claimed in claim 1, wherein the reaction is carried out at from 400° to 700° C.

5. A process as claimed in claim 1, wherein the reaction is carried out at from 0.001 to 40 bar.

6. A process as claimed in claim 1, wherein the reaction is carried out using a reaction tube of diameter from 20 to 1,000 millimeters and length from 100 to 2,000 millimeters, containing packings of from 10 to 50 millimeters diameter.

7. A process as claimed in claim 1, wherein the reaction is carried out using a solvent which is inert under the reaction conditions.

* * * * *

UNITED STATES PATENT AND TRADEMARK OFFICE
CERTIFICATE OF CORRECTION

PATENT NO. : 4,322,365
DATED : March 30, 1982
INVENTOR(S) : Franz Merger and Friedrich Towae It is certified that error appears in the above–identified patent and that said Letters Patent are hereby corrected as shown below:

Column 5, lines 51-53,
please correct Formula I to read:

-- $R^1 - N = C = O$ --.

*Signed and Sealed this*

*Twenty-fifth* Day of *January 1983*

[SEAL]

Attest:

GERALD J. MOSSINGHOFF

Attesting Officer

Commissioner of Patents and Trademarks